United States Patent [19]
Patry

[11] Patent Number: 4,989,733
[45] Date of Patent: Feb. 5, 1991

[54] READY-TO-USE MEDICAL TRAYS

[76] Inventor: Marc Patry, 60, du Chanoine-Groulx, Vaudreuil, Quebec, Canada, J7V 2V2

[21] Appl. No.: 525,668

[22] Filed: May 21, 1990

[51] Int. Cl.$^5$ .................... B65D 1/36; B65D 85/62
[52] U.S. Cl. .................... 206/570; 206/210; 206/438; 206/440; 206/561
[58] Field of Search ............ 206/438, 439, 440, 205, 206/561, 570, 210, 363, 370

[56] References Cited

U.S. PATENT DOCUMENTS

| | | | |
|---|---|---|---|
| 2,613,862 | 10/1952 | Vaughn | 206/205 X |
| 3,061,087 | 10/1962 | Scrivens et al. | 206/439 |
| 3,435,948 | 4/1969 | Kaganov et al. | 206/439 |
| 3,465,873 | 9/1969 | Munz | 206/205 |
| 3,481,462 | 12/1969 | Chapel | 206/438 |
| 3,534,887 | 10/1970 | Ginsberg | 206/812 X |
| 3,613,685 | 10/1971 | Reynolds | 604/289 |
| 3,717,533 | 2/1973 | Mayworm et al. | 206/439 X |
| 3,770,119 | 11/1973 | Hultberg et al. | 206/558 |
| 3,954,174 | 5/1976 | Kraus | 206/439 |
| 3,987,895 | 10/1976 | Jamshidi | 206/564 |
| 4,022,324 | 5/1977 | Schuster | 206/210 X |
| 4,128,173 | 12/1978 | Lazarus et al. | 206/570 |
| 4,160,505 | 7/1979 | Rauschenberger | 206/564 |
| 4,195,734 | 4/1980 | Boner et al. | 206/558 |
| 4,444,310 | 4/1984 | Odell | 206/363 X |
| 4,482,053 | 11/1984 | Alpern et al. | 206/439 |
| 4,501,363 | 2/1985 | Isbey, Jr. | 206/570 |
| 4,522,302 | 6/1985 | Paikoff | 206/570 |
| 4,595,102 | 6/1986 | Cianci et al. | 206/370 X |
| 4,901,851 | 2/1990 | Gerry | 206/210 X |
| 4,954,239 | 9/1990 | Mueller | 206/210 X |

Primary Examiner—William I. Price
Attorney, Agent, or Firm—Robic

[57] ABSTRACT

Ready-to-use medical trays for retaining preparations. A tray for parturient comprises a first cell for retaining at least one sponge or cloth impregnated with a disinfectant. A second cell comprises at least one sponge or cloth impregnated with a disinfectant. This disinfectant is for a chirurgical intervention. The tray comprises also sealing closure for sealing its top and thereby each of the cells individually. Other trays comprise 3 cells for washing, drying and disinfecting skin and 4 cells for gynecological incursion.

20 Claims, 4 Drawing Sheets

READY-TO-USE MEDICAL TRAYS

FIELD OF THE INVENTION

This invention relates to ready-to-use medical trays for retaining medical preparations, and in particular for ready-to-use trays having easy-peel-off tabs to be directly used in operating rooms.

BACKGROUND OF THE INVENTION

Trays containing a package of sterile sponges have been described by Scrivens et al. in U.S. Pat. No. 3,061,087 dated Oct. 30, 1962. Reynolds in U.S. Pat. No. 3,613,685, dated Oct. 19, 1971 describes trays containing surgical preparations. Other trays have been described by Kraus in U.S. Pat. No. 3,954,174, dated May 4, 1976 for unitary two-compartment package for sterile surgical articles and by Hultberg et al. in U.S. Pat. No. 3,770,119, dated Nov. 6, 1973, for trays having a raised rim about their periphery and a sterile drape attached to the tray body and folded together with the rim and with possibilities of auxiliary trays. Other trays are known but for very specific purposes, such as liver biopsy tray, denture care tray, catheterization tray or for transporting medication or the like tray, such as described in U.S. Pat. No. 4,195,734 by Boner et al.

SUMMARY OF THE INVENTION

The invention aims at producing kits for retaining medical preparations particularly ready-to-use trays for operating rooms or for other medical uses, although such trays could be used for other skin preparations.

Broadly stated, the invention is directed to a ready-to-use medical tray for retaining medical preparations, said tray comprising a first cell for retaining at least one member selected from the group consisting of sponges or cloths impregnated with a disinfectant, a second cell for retaining a member selected from the group consisting of at least one member selected from sponges or cloths impregnated with a disinfectant, for applying said disinfectant for a surgical intervention, said tray further comprising a sealing closure for sealing the top of said tray and thereby each of said cells individually.

Broadly stated, the invention is also directed to a ready-to-use medical tray for retaining general surgery preparation, said tray having a first cell for retaining at least one member selected from the group consisting of sponges or cloths impregnated with detergent and disinfectant, and a second cell for retaining at least one member selected from the group consisting of sponge or cloth for drying purposes and a third cell containing at least one member selected from the group consisting of sponges and clothes for applying a disinfectant, said tray further comprising a sealing closure for sealing the top of said tray and thereby each of said cells individually. The tray may also contain a fourth cell and other elements as will be described hereinbelow.

BRIEF DESCRIPTION OF THE DRAWINGS

In the drawings which illustrate preferred embodiments of the invention.

DETAILED DESCRIPTION OF THE DRAWINGS

Figure 1:
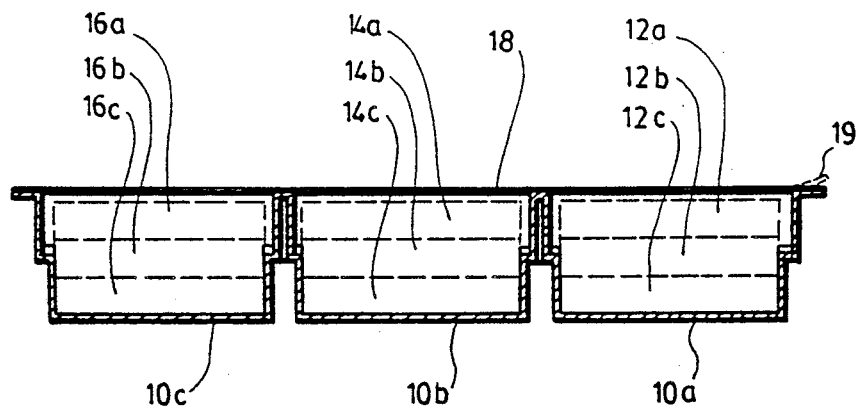
FIG. 1 is a cross-sectional view taken along the length of a 3-cell tray for general surgical end uses.
Figure 2:
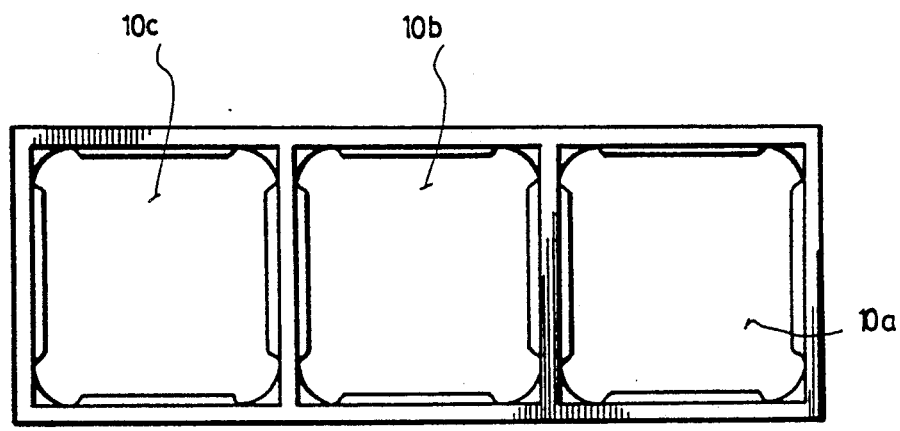
FIG. 2 is a top view of the tray shown in FIG. 1.

Referring now to FIGS. 1 and 2, the tray 10 comprises 3 cells 10a, 10b and 10c. In the first cell 10a, sponges such as shown in 12a, 12b and 12c are saturated with disinfectant, detergent and water. In the second cell 10b, absorbing sponges 14a, 14b, 14c are contained in cell 10b to dry the skin after washing with the sponges 12a, 12b and 12c. In the third cell 10c, the sponges 16a, 16b, 16c contain a disinfectant to sterilize the skin. The 3 cells are sealed by a membrane 18 which individually seals each of the 3 cells. The membrane 18 may be advantageously provided with an easy-peel-off tab 19.

The sponges are preferably highly absorbent. Polyurethane sponges having a high porosity to retain liquid may be used for instance.

The tray may conveniently be a thermoformable, such as polystyrene, polyethylene, polypropylene polyester trays, other thermoformable material may also be used, for instance polyvinyl chloride if one so wishes.

Figure 3:
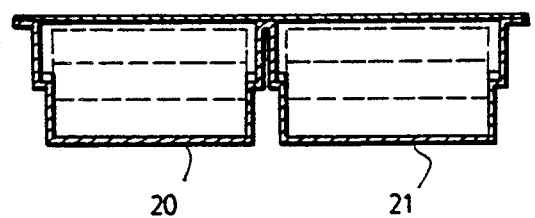
FIG. 3 is another cross-sectional view of another preferred tray having two cells for caesarean section.

Referring now to FIG. 3, the tray comprises two cells 20, 21 containing sponges, advantageously 3 sponges on each cell, the sponges being saturated with a aqueous disinfectant solution. Such a kit may be used for instance for the preparation of parturient for caesarean section.

Figure 4:
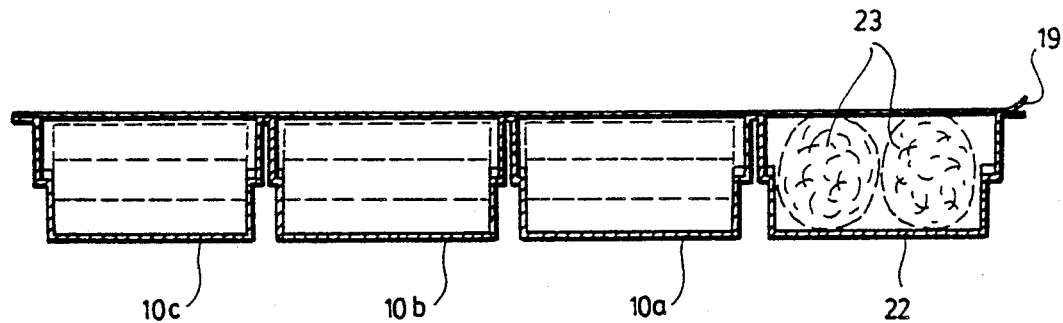
FIG. 4 is another cross-sectional view of another tray having four cells for gynaecological end uses.

Referring now to FIG. 4, the tray comprises a tray similar to the one shown on FIGS. 1 and 2, except that a fourth cell 22 is provided for receiving a plurality of balls 23 of medical cotton-wool containing a disinfectant. This tray is conveniently used for gynaecological incursion.

Figure 5:
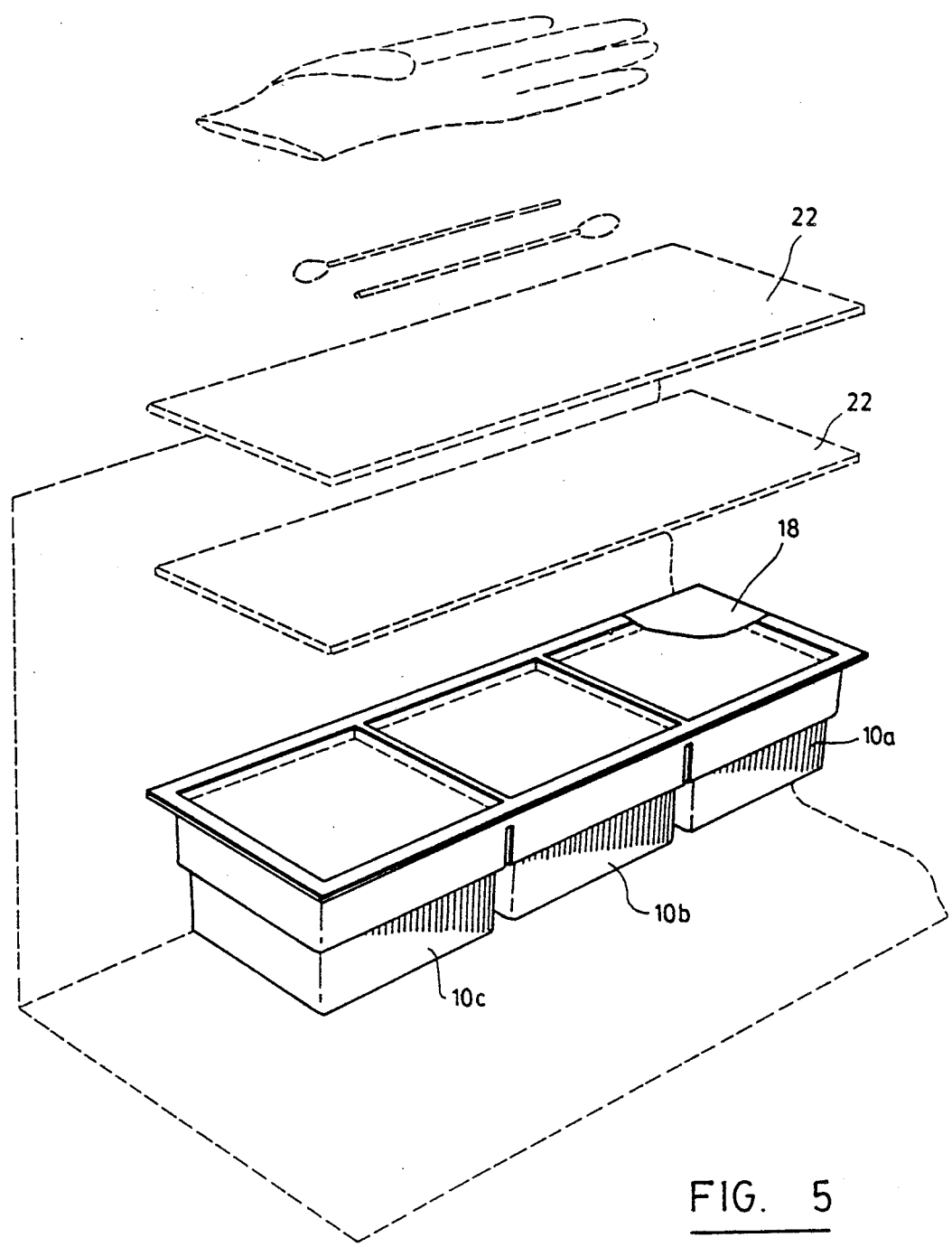
FIG. 5 is an exploded view of another version of a tray as shown in FIG. 1.

Referring now to FIG. 5, the tray 10 having 3 cells 10a, 10b and 10c as defined above and sealed with membrane 18 are provided on the top of membrane 18 with one or more towels 22 and at least one glove to be wrapped in a cloth or paper and sterilized. The wrapping may also contain a plurality of sticks having at at least one of their ends cotton-wool. The wrapping is then inserted in a plastic bag to keep said wrapping away from dust. If desired, the tray as shown in FIG. 3 or 4, instead of the tray shown in FIG. 5, may be used.

Figure 6:
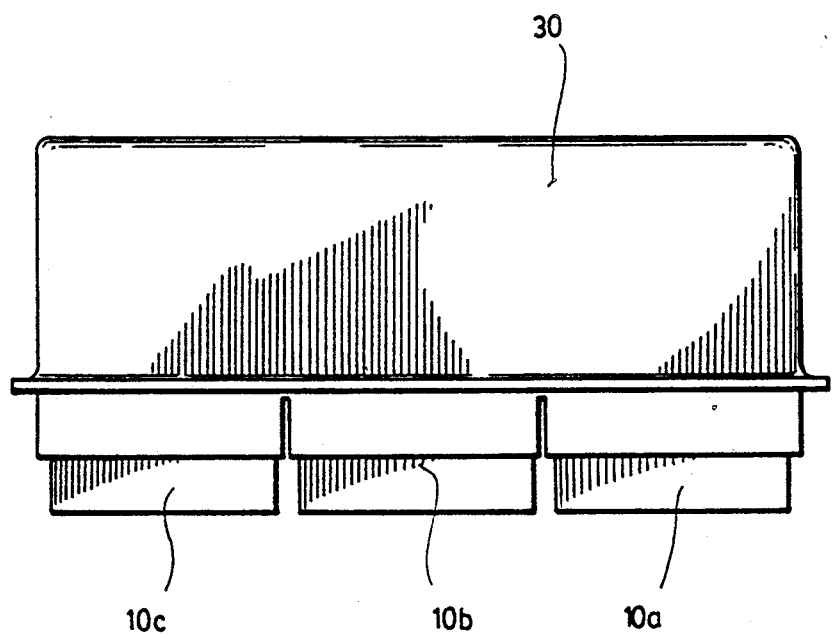
FIG. 6 is still another version of a tray as shown in FIG. 1.

As shown in FIG. 6, if one wishes, instead of having a wrapping, a cover 30 may be provided to securely engage the sides of the tray 10, said top comprising at least some of the elements described in FIG. 5.

Any or all of the sponges described above may be replaced with cloths and the like, if desired, as the substrate containing the water-detergent, or the disinfectant or for drying the skin. However, high retention sponges are by for the most preferred substrate to carry out the preparations and the cloths are only a second choice.

As examples of disinfectant that one may wish to use are chlorhexidine gluconate, povidone-iodine.

As a way of example in a particular embodiment using a tray as described in FIG. 1, in the first cell the sponges contain in a first example, chlorhexidine gluconate 2-4% aqueous with a detergent.

In a second example, a cleaning solution containing 7.5% of povidone-iodine solution of which 0.75% is free iodine the remaining portion being sterilized water.

Other examples include hexachlorophenes, polyvinylpyrollidone complex containing iodine and iodophore containing 0.5% iodine.

As examples of disinfectant for tray 3 of FIG. 1 or tray of FIG. 3, one may use a 20% aqueous sterilized solution of chlorhexidine gluconate or a 10% povidone-iodine aqueous solution. The aqueous solution may contain up to 70% isopropanol.

When as indicated in FIG. 1, a cell such as the second cell, contains a drying sponge or the like, ethylene oxide in the presence of a carrier such as methanol may be used as a sterilizing active substance. Indeed, ethylene oxide may be used in any of the cells as a sterilizing active substrate, if one so wishes. Also the sponge may contain water or aqueous solution of alcohol to assist drying for instance isopropanol.

In a preferred embodiment as shown in FIGS. 2 and 1, the upper portion of the cells are enlarged to ease removal and replacement of sponges.

In another preferred embodiment, the sponges are about 7×7 cm and 1 cm thickness.

Preferably, the sponges are slightly smaller than the dimension of the cells. The cells have preferably the same conformation as the sponges but need not have. Indeed the cells may have various configurations.

In a preferred embodiment, the sponges have the following characteristics:

| DENSITY | |
|---|---|
| lbs./cu. ft. | 1.75–1.90 |
| kgs./m$^3$ | 28–31 |
| INDENTATION LOAD DEFLECTION | |
| lbs. at 25% | 40–44 |
| kgs. at 25% | 18–20 |
| TENSILE STRENGTH | minimum 9 |
| lbs./sq. ins. | |
| ELONGATION | 150 |
| % minimum | |
| COMP SET | 12 |
| 90% maxium | |
| COMP MODULUS | 1.9 |
| minimum | |
| HYSTERESIS LOSS | 30 |
| % maximum | |

RESILIENCY % minimum 40

According to:
1. A.S.T.M. 3574-77
2. A.S.T.M. D3574
3. D.O.T. M.V.S.S. #302
4. California Technical Bulletin #117 sections A & D
5. Can 2-4.2-M77. Method 27.7- 1979

A capacity of absorption for liquid of at least 50% by weight is preferred.

These trays are readily used in operating rooms without the necessity to carry various bottles, and other equipment for their disposals.

The membrane sealing such as 18 may be a paper-polymer or a polymer closure.

Although the present invention has been explained hereinabove by way of preferred embodiments thereof, it should be pointed out that any modifications to these preferred embodiments, within the scope of the appended claims, is not deemed to change or alter the nature and scope of the invention.

We claim:

1. A ready-to-use medical tray for retaining medical preparations, said tray comprising a first cell for retaining at least one member selected from the group consisting of sponges or cloths impregnated with a disinfectant, a second cell for retaining a member selected from the group consisting of at least one member selected from sponges or cloths impregnated with a disinfectant, for applying said disinfectant for a surgical intervention, said tray further comprising a sealing closure for sealing the top of said tray and thereby each of said cells individually.

2. The tray as defined in claim 1 for preparation in a caesarean section.

3. The tray as defined in claim 1, further including a top portion containing gloves.

4. A ready-to-use medical tray for retaining general surgery preparation, said tray having a first cell for retaining at least one member selected from the group consisting of sponges or cloths impregnated with detergent and disinfectant, and a second cell for retaining at least one member selected from the group consisting of sponge or cloth for drying purposes and a third cell containing at least one member selected from the group consisting of sponges and clothes for applying a disinfectant, said tray further comprising a sealing closure for sealing the top of said tray and thereby each of said cells individually.

5. A ready-to-use medical general surgery preparation, said tray having a first cell for retaining at least one sponge impregnated with detergent and disinfectant, a second cell for retaining at least one sponge for drying purposes, and a third cell containing at least one sponge for applying a disinfectant, said tray further comprising a sealing closure for sealing the top of said tray and thereby each of said cells individually.

6. The tray as defined in claim 5, wherein said first and third cell contain sponges retaining as a disinfectant at least one member selected from the group consisting of chlorhexidine gluconate and povidone iodine.

7. The tray as defined in claim 5, wherein said sponge for drying purposes contains a residual amount of alcohol.

8. The tray as defined in claim 7, wherein said alcohol is isopropanol.

9. The tray as defined in claim 8, wherein said isopropanol is a slightly aqueous solution.

10. The tray as defined in claim 1, wherein said tray is a thermomoldable tray.

11. The tray as defined in claim 1, wherein said member is selected from polyurethane sponges having a high retention capacity.

12. The tray as defined in claim 1, wherein said sealing closure is member selected from the group comprising a paper-polymer and polymer closures.

13. The tray as defined in claim 5, which includes a fourth cell, said fourth cell containing balls of medical cottonwool containing a disinfectant.

14. The tray as defined in claim 5, containing ethyleneoxide.

15. A tray as defined in claim 5, being sterilely wrapped with at least one towel, at least one glove, and at least one stick, said stick having wrapped at at least one of its ends with cotton-wool.

16. The tray as defined in claim 15, wherein said tray is sterilely wrapped with sterile paper or cloth.

17. The tray as defined in claim 1, wherein said sealing closure includes an easy-peel-off tab.

18. The tray as defined in claim 5, wherein said tray is a thermomoldable tray.

19. The tray as defined in claim 5, wherein said sealing closure is a member selected from the group comprising paper-polymer and polymer closures.

20. A tray as defined in claim 1, being sterilely wrapped with at least one towel, at least one glove, and at least one stick, said stick having wrapped at at least one of its ends with cotton-wool.

* * * * *